United States Patent [19]

Yamamoto et al.

[11] Patent Number: 5,069,678
[45] Date of Patent: Dec. 3, 1991

[54] DISPOSABLE DIAPERS

[75] Inventors: Masamitsu Yamamoto, Kawanoe; Noriyuki Kimura, Iyomishima; Yoshihisa Fujioka, Kagawa; Hiroki Yamamoto; Makoto Suekane, both of Kawanoe, all of Japan

[73] Assignee: Uni-Charm Corporation, Ehime, Japan

[21] Appl. No.: 588,759

[22] Filed: Sep. 27, 1990

[51] Int. Cl.⁵ .............................................. A61F 13/15
[52] U.S. Cl. .................................. 604/385.1; 604/358
[58] Field of Search ................... 604/385.1, 385.2, 358, 604/386-389, 400

[56] References Cited

U.S. PATENT DOCUMENTS

| | | | |
|---|---|---|---|
| 2,366,002 | 12/1944 | Carden | 604/386 |
| 2,523,989 | 3/1949 | Geeslin | 604/385.1 |
| 2,544,620 | 3/1951 | Steinert | 604/385.1 |
| 4,501,587 | 2/1985 | Enloe | 604/385.1 |

*Primary Examiner*—Randy Citrin Shay
*Assistant Examiner*—Gina Gualtieri
*Attorney, Agent, or Firm*—Fred Philpitt

[57] ABSTRACT

Here is disclosed a disposable diaper having a front area, a crotch area, a back area and a pair of liquid permeable wing areas laterally extending from opposite sides of said back area so that said diaper may be worn by fastening said wing areas to each other, then placing said front area upon these wing areas and fastening said front area to said wing areas.

2 Claims, 4 Drawing Sheets

DISPOSABLE DIAPERS

BACKGROUND OF THE INVENTION

This invention relates to disposable diapers adapted to receive excretions and more particularly to such disposable diapers suitable for adult users.

Most of the conventionally available diapers for adult users are characterized in a substantially T-shaped configuration as a whole defined by a back area and a pair of wing areas laterally extending from opposite sides of the back area.

Diapers of such configuration are generally classified into two types depending upon the sequence for wearing them when the wearer is in bed.

With the first type, an attendant places a back area of a diaper on the rear waist of the wearer, places a crotch area thereof on the crotch of the wearer with a front area thereof being held in hand, places said front area on the belly of the wearer and finally places and fastens said wing areas one on another over the belly of the wearer. Most of the conventional diapers are of this first type so far as the sequence for wearing is concerned.

With the second type, the attendant places a back area of a diaper on the rear waist of the wearer, fastens wing areas thereof one on another over the belly of the wearer, places a crotch area thereof on the crotch of the wearer with a front area thereof held in hand, places said front area on the belly of the wearer so as to cover said wing areas and finally fastens said front area onto said wing areas.

Concerning the ease for the diaper to be worn, the latter is better than the former, because, with the latter type, the diaper is fastened around the waist of the wearer at the intermediate step of wearing by coupling said wing areas to one another over the belly of the wearer and the diaper can be worn by the wearer him- or herself who stands up.

With the latter type, however, an absorbent core located in said front area would not be effectively utilized for absorption of liquid excretions since a liquid-impermeable backsheet extends over the entire diaper including said wing areas. Specifically, said front area is placed upon said wing areas having the liquid-impermeable backsheet and these wing areas form a barrier against permeation of liquid excretions into said front area. When said front area is not effectively utilized for absorption of liquid excretions in this manner, the liquid absorption capacity in said front area will be insufficient to avoid undesirable leakage of liquid excretions, particularly when the wearer is adult. Leakage due to such insufficient liquid absorption capacity in said front area often occurs particularly when the wearer is male or when the wearer is female and laying on her own side on the bed.

It is an object of the invention to provide disposable diapers which are of the foregoing second type but constructed so that the front area of diaper also has a sufficient liquid absorption capacity.

SUMMARY OF THE INVENTION

The object set forth above is achieved, in accordance with the invention, by a disposable diaper comprising a liquid permeable topsheet covering a front area, a crotch area and a back area, a liquid-impermeable backsheet covering these areas, an absorbent core sandwiched between these sheets, and a pair of wing areas laterally extending from opposite sides of said back area, wherein said diaper is worn by fastening said wing areas to each other, then placing said front area upon these wing areas and fastening said front area to said wing area, characterized in that said wing areas are made of material having a liquid permeability in the direction of their thickness.

In a preferred embodiment, said wing areas are constructed from a liquid-permeable topsheet, a liquid-permeable backsheet and a liquid absorbent core sandwiched between these sheets.

In another preferred embodiment, particularly when said wing areas are provided therein with no absorbent core, a liquid absorption capacity per $m^2$ of said core in said front area is adjusted to be higher than those in the other areas.

According to the invention, although the wearing sequence corresponds to the foregoing second type, i.e., the wing areas are folded on each other and thereafter the front area is folded on these wing areas, the portion of the liquid absorbent core occupying the front area satisfactorily absorbs the quantity of liquid excretions having permeated through said wing areas, since said wing areas are liquid-permeable.

When the wing areas also are provided therein with the liquid absorbent core, liquid excretions are absorbed not only by the portion of the liquid absorbent core occupying said front area but also by the portion of the liquid absorbent core occupying these wing areas.

Consequently, the front area is effectively utilized for absorption of liquid excretions, eliminating the problem of prior art that the insufficient liquid absorption capacity causes the undesirable leakage of liquid excretions. Particularly when the wearer is male or when the wearer is female and laying on her own side on the bed, a sufficient liquid absorption capacity can be assured in the front area.

The invention is based on the previously mentioned second type of conventional disposable diapers for adult users adapted to be worn folding fastened the wing areas on each other to immobilize a diaper around the waist of the wearer, followed by folding the front area on these wing areas. Therefore, the diaper can be easily and reliably worn with help of the attendant or even by the wearer him- or herself. Furthermore, the attendant can check whether there are excretions or not simply by opening the front area leaving the wing areas fastened to each other so as to prevent the diaper from any displacement from its initial position and, after checking, can rapidly fold the front area back onto the wing areas.

PREFERRED EMBODIMENTS

Figure 1:
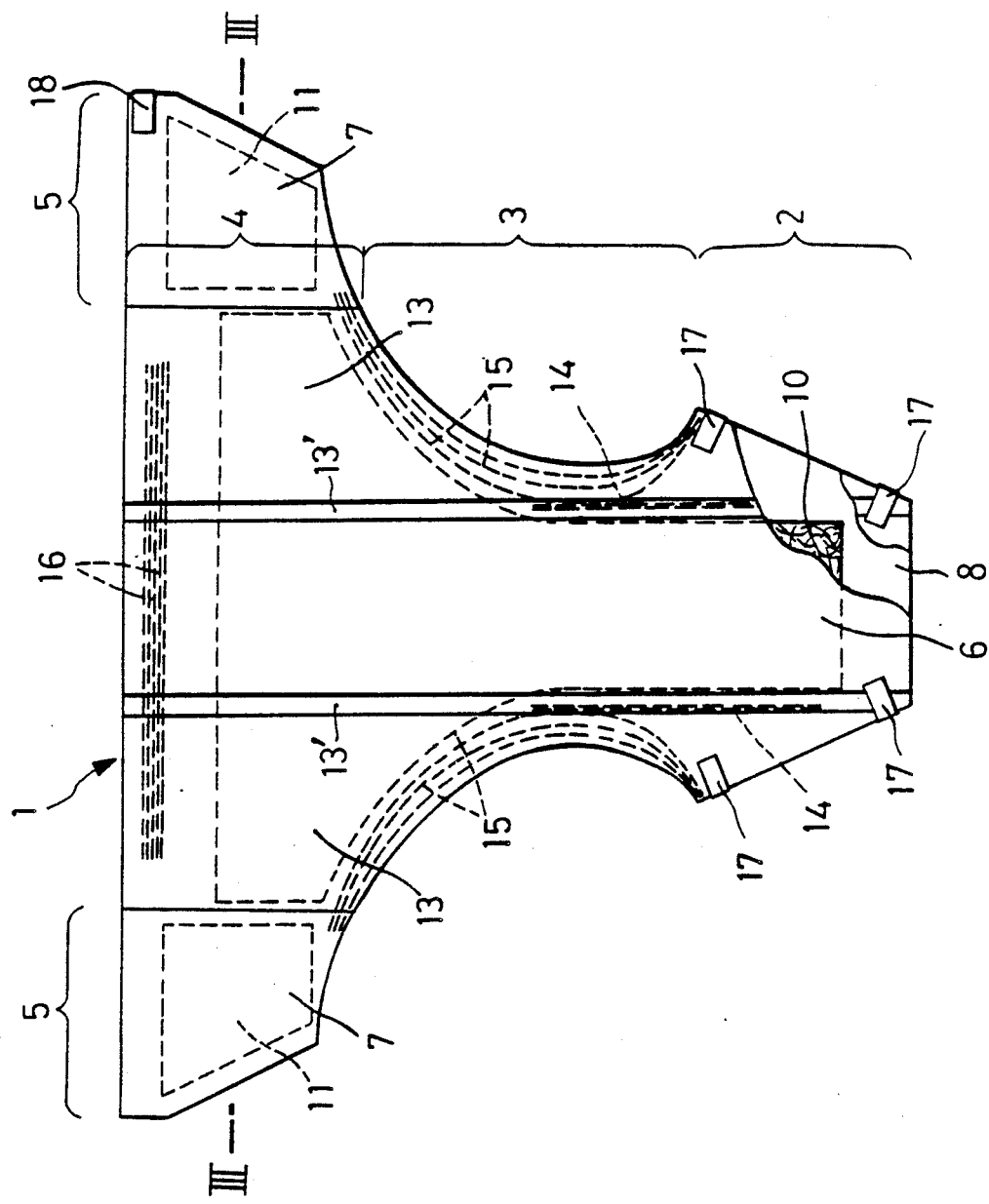
FIG. 1 is a developed plan view partially broken away of an embodiment of the invention as viewed toward the inner side (upper side) thereof.
Figure 2:
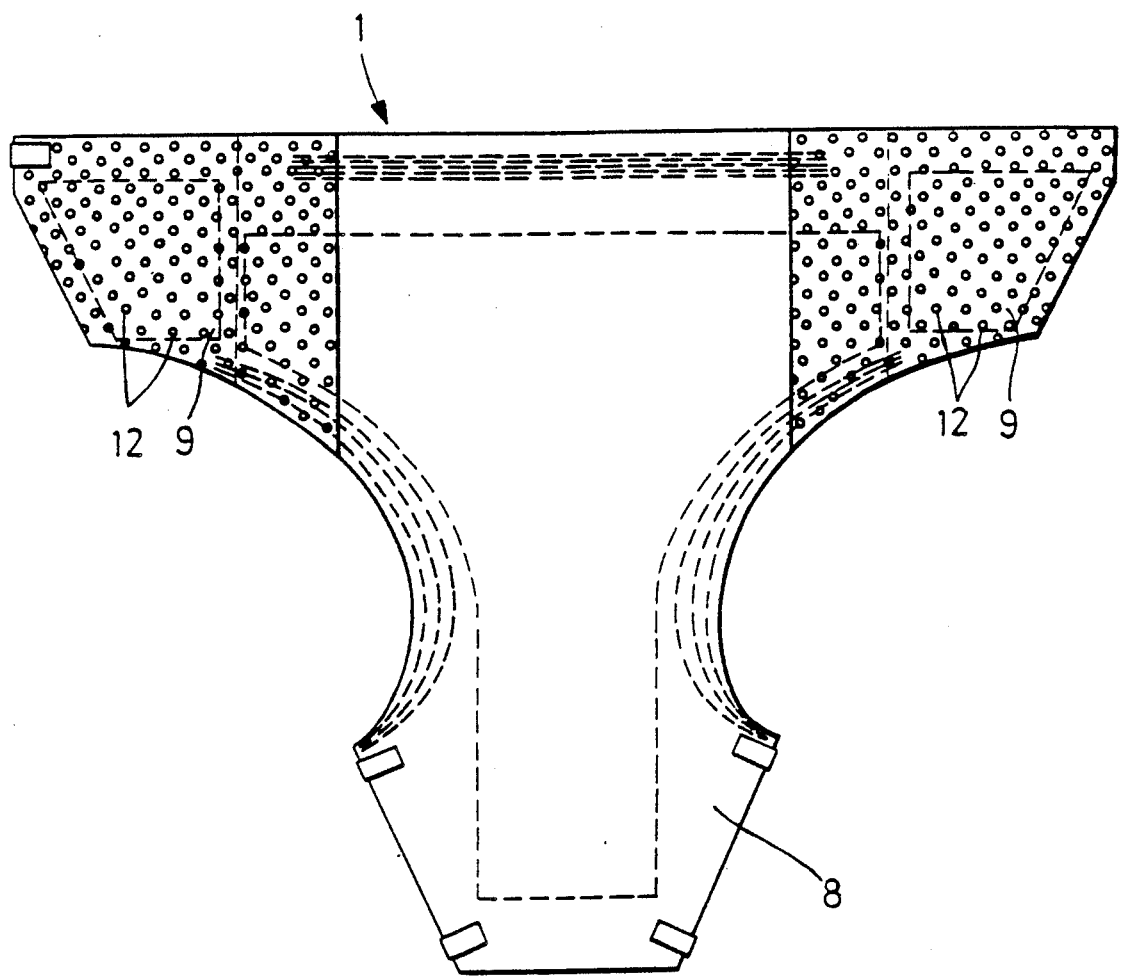
FIG. 2 is a view similar to FIG. 1 as viewed toward the outer side (lower side) thereof.
Figure 3:
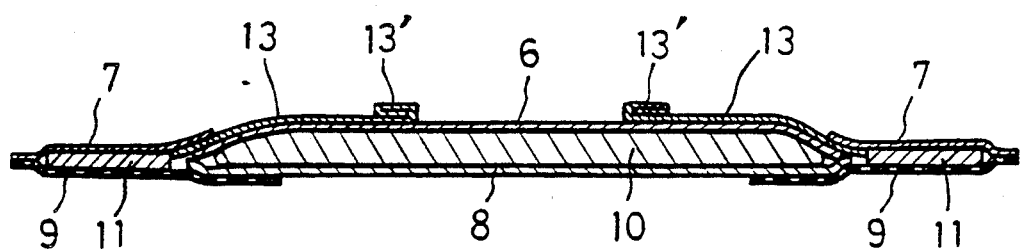
FIG. 3 is a sectional view taken along a line III—III in FIG. 1.
Figure 4:
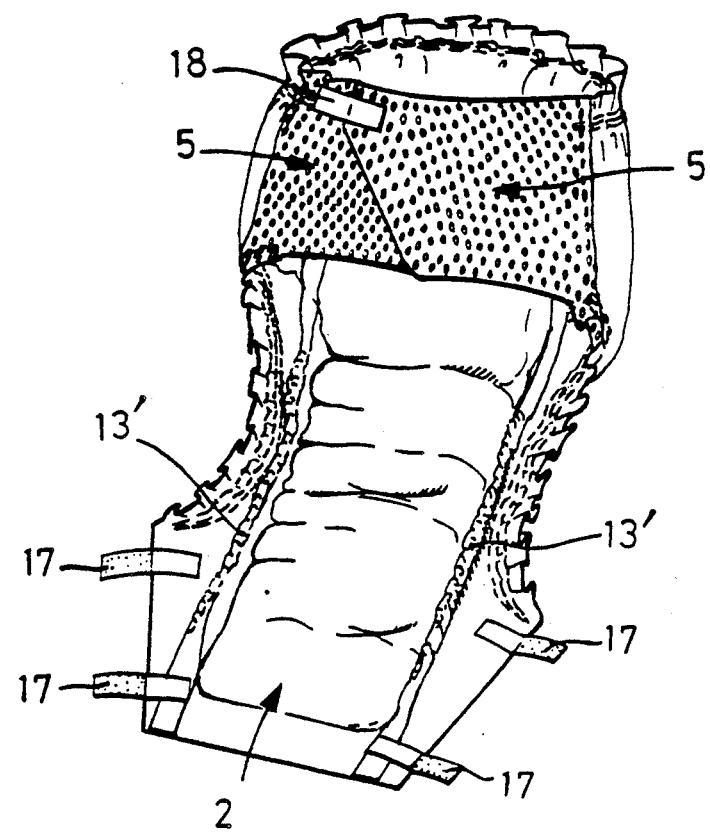
FIG. 4 is a perspective view of such diaper at an intermediate step of its wearing sequence.

The invention will be described by way of example in reference with the accompanying drawings.

Referring to FIGS. 1 through 4, a diaper proper 1 has a front area 2, a crotch area 3, a back area 4, and a pair of wing areas 5 laterally extending from opposite sides of the back area 4. The diaper proper 1 comprises a first liquid-permeable topsheet 6 covering the front area 2, the crotch area 3 and the back area 4, second liquid-permeable topsheets 7 covering the wing areas 5, a first liquid-impermeable backsheet 8 covering the front area 2, the crotch area 3 and the back area 4, second liquid-impermeable backsheets 9 covering the wing areas 5, a first liquid absorbent core 10 sandwiched centrally between the first topsheet 6 and the first backsheet 8 and second liquid absorbent cores 11 sandwiched between the respective second topsheets 7 and the respective second backsheets 9. Each of the second cores 11 is thinner than the first core 10 and may be also integral with said first core 10 although the second cores 11 are shown as being formed separately of the first core 10. The second topsheets 7 are joined to the first topsheet 6 by respective side sheets 13 and the second backsheets 9 are joined directly to the first backsheet 8, respectively, with use of suitable adhesive or welding means. The second backsheets 9 are provided with fine perforations 12. Laterally opposite sides of the top- and backsheets 6, 8 and the first core 10 are inwardly curved along the crotch area 3. The first core 10 laterally extends in the back area 4 and defines a substantially T-shape.

On an upper surface of the diaper proper 1, i.e., on an upper surface of the topsheet 6, in a longitudinally central zone thereof, there are provided a pair of elastic narrow sidesheets 13 so as to be opposed to both sides of the front area 2, the crotch area 3 and the back area 4, and outer sides of the respective sidesheets 13 are joined to the upper surface of the topsheet 6. The sidesheets 13 are endowed with their elasticity by elastic members 14 wrapped in inner edge sleeves 13' of the respective sidesheets 13. While the respective sidesheets 13 are shown with inner ends thereof being collapsed outward and joined onto the topsheet 6, it is also possible to collapse said inner ends inward and to join them onto the topsheet 6 or to collapse one end inward and the other end outward and to join them onto the topsheet 6.

The diaper proper 1 is provided with elastic members 15 extending along the opposite edges in the crotch area 3 and with an elastic member 16 extending along the upper edge of the back area 4, both elastic members 15, 16 being sandwiched between the top- and backsheets 6, 8.

The diaper proper 1 is further provided at four corners in the front area 2 with pressure sensitive tapes 17, respectively, and at an upper corner in one of the wing areas 5 with a pressure sensitive tape 18.

Figure 5:
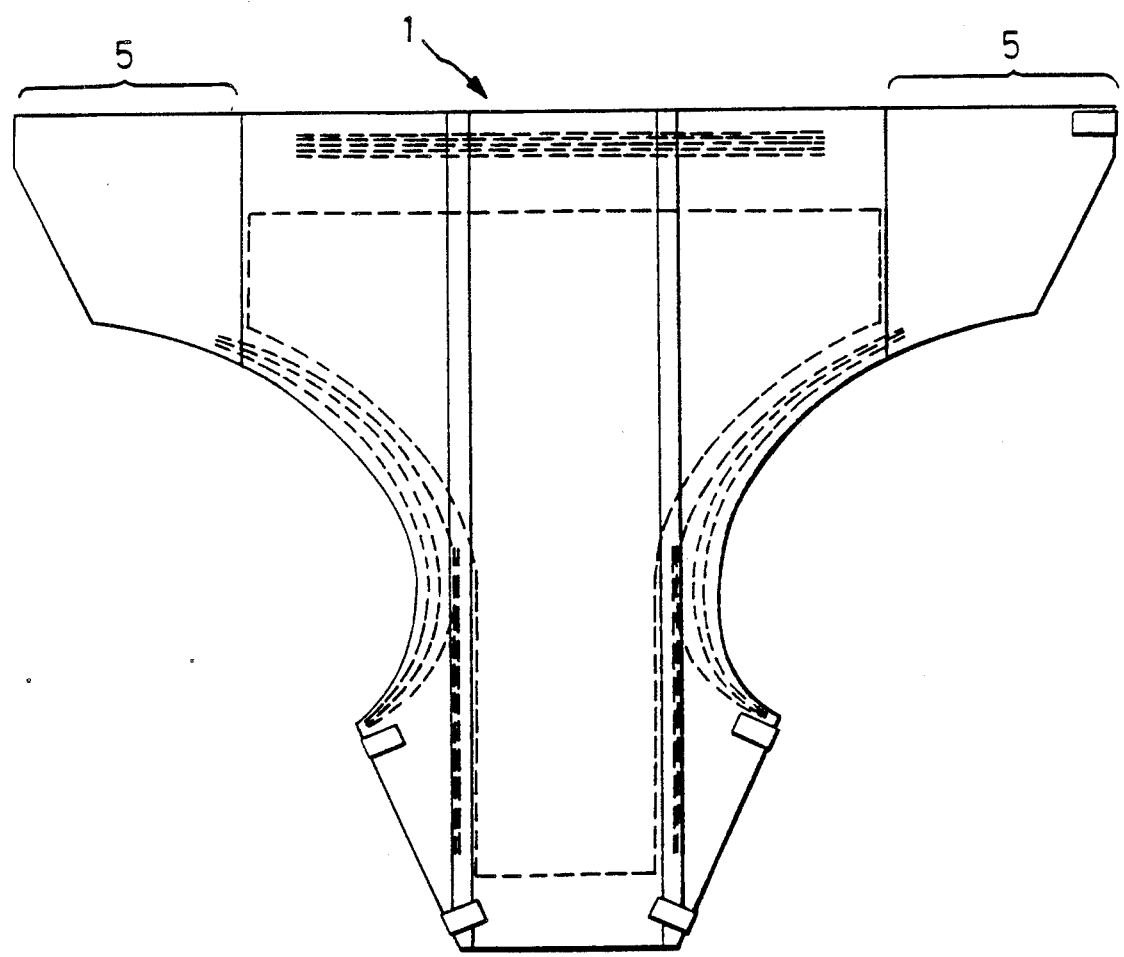
FIG. 5 is a view similar to FIG. 1 of another embodiment of the invention.

Referring to FIG. 5, another embodiment of the invention having none of the second cores 11 is shown. Remainder of the construction is similar to the previous embodiment. In this embodiment, however, it is also possible to construct each of the wing areas from a single layer of porous sheet. It is preferred in this embodiment that the first core 10 has weight per $m^2$ heavier in the front area 2 than in the other areas to assure a sufficient liquid absorption capacity.

Obviously, contour of the diaper proper 1 in the front area 2 and the wing areas 5 may be other than those as shown.

Preferably, the first and second topsheets 6, 7 are made of nonwoven fabric, the first backsheet 8 is made of plastic film, the second backsheet 9 is made of open plastic film or open nonwoven fabric, the first and second cores 10, 11 are made of fluffy pulp and superabsorptive polymer particles, and the sidesheets 13 are made of nonwoven fabric. However, particular materials are not critical.

Now a sequence in which a disposable diaper constructed as has been mentioned according to the invention will be described. The attendant places the back area 4 on the back waist of the wearer, then folds the wing areas 5 on each other so that the one wing area 5 having the tape fastener 18 overlies the other wing area 5 over the belly of the wearer and secures the tape fastener 18 to the other wing area 5. Thereafter the attendant places the crotch area 3 on the crotch of the wearer with the front area 2 being held in hand and places the front area 2 over the belly of the wearer so as to cover the wing areas 5. Finally, the attendant secures the tape fasteners 17 of said front area to said wing areas.

When a diaper of the invention is worn by the wearer him- or herself, the sequence as has been mentioned may be followed by the wearer who is standing up.

What is claimed is:

1. A disposable diaper that comprises
(A) a first central portion having two sides that consists of
 (a) a front area (2), a back area (4) and a crotch area (3) that connects said front and back areas,
 (b) a liquid-permeable topsheet (6) covering one side of said first central portion and which is adapted to be placed against the body of the wearer,
 (c) a liquid-impermeable backsheet (8) covering the other side of said first central portion and which is not adapted to be placed against the body of a wearer, and
 (d) a first liquid absorbent core (10) sandwiched between said topsheet (6) and said backsheet (8),
(B) two spaced apart wing portions (5)
 (a) each wing portion extending laterally outwardly from opposite sides of the back area (4) of said first central portion,
 (b) each wing portion being composed of a second liquid absorbent core (11) sandwiched between two liquid permeable sheets (7, 9),
(C) first fastening means (18) associated with said wing portions (5) so that when the wing portions (5) are folded toward each other they can be fastened to each other in an overlapping relationship, and
(D) second fastening means (17) on said first central portion so that after said wing portions (5) have been fastened to each other in an overlapping relationship by fastening means (18) said front area (2) can be fastened to said back area (4) with the overlapped wing portions (5) therebetween.

2. A disposable diaper as set forth in claim 1 wherein the liquid absorption capacity per $m^2$ of said first liquid absorbent core (10) is greater than that of said second liquid absorption core (11).

* * * * *

UNITED STATES PATENT AND TRADEMARK OFFICE
CERTIFICATE OF CORRECTION

PATENT NO. : 5,069,678
DATED : December 3, 1991
INVENTOR(S) : Masamitsu YAMAMOTO et al It is certified that error appears in the above-identified patent and that said Letters Patent is hereby corrected as shown below:

Add the following

ON THE TITLE PAGE:

[30]    Foreign Application Priority Data

October 5, 1989 [JP]   Japan .... 1-261837

Signed and Sealed this

Second Day of November, 1993

Attest:

BRUCE LEHMAN

*Attesting Officer*    *Commissioner of Patents and Trademarks*